US005538900A

United States Patent [19]

Rooney

[11] Patent Number: 5,538,900
[45] Date of Patent: Jul. 23, 1996

[54] ASSESSMENT OF CHARACTERISTICS OF FLUIDS

[75] Inventor: Matthew J. Rooney, West Bridgford, United Kingdom

[73] Assignee: Naked Eye Limited, St. Hellier, Channel Islands

[21] Appl. No.: 256,654

[22] PCT Filed: Jan. 22, 1993

[86] PCT No.: PCT/GB93/00151

§ 371 Date: Aug. 29, 1994

§ 102(e) Date: Aug. 29, 1994

[87] PCT Pub. No.: WO93/15390

PCT Pub. Date: Aug. 5, 1993

[30] Foreign Application Priority Data

Jan. 22, 1992 [GB] United Kingdom ............ 9201348

[51] Int. Cl.⁶ ..................................... G01N 21/03
[52] U.S. Cl. ............... 436/165; 436/63; 436/66; 422/55; 422/58; 422/82.05; 422/102
[58] Field of Search ............ 436/165, 63, 66; 422/55, 58, 82.05, 99, 102

[56] References Cited

PUBLICATIONS

Fiddik et al. "A variable pathlength . . ." Journal of Physics E. Scientific Instruments vol. 21, No. 11, Nov. 1988.
Airsschfeld "Lens and Wedge . . ." Applied Spectroscopy vol. 39, No. 3 Jun. 1985.

JP Abstract vol. 009, No. 24 (p. 331) 31 Jan. 1985 Hitachi Densenkk.

*Primary Examiner*—James C. Housel
*Assistant Examiner*—Rachel Heather Freed
*Attorney, Agent, or Firm*—Galgano & Burke

[57] ABSTRACT

A method of, and apparatus for, assessing a characteristic of a fluid, particularly for assessing the degree of contamination of a fluid by a substance which causes the fluid to become progressively less transparent to radiation with increasing contamination, wherein the fluid is introduced into a chamber, and the attenuation of the radiation by passage through the fluid in the chamber at the different parts therein is examined. The invention is particularly applicable to assessment of contamination of a mainly aqueous liquid by blood, and the apparatus comprises a container with walls approaching one another towards one part of the container, and a visible marking such as a pattern and/or graduated scale behind the rear wall of the container to be looked at through the liquid in the container by a user, the arrangement being such that the point where the making becomes invisible to the user provides a measure of the contamination.

17 Claims, 2 Drawing Sheets

ASSESSMENT OF CHARACTERISTICS OF FLUIDS

This invention relates to a method of, and apparatus for, assessing characteristics of fluids. More particularly, it relates to the quantitative assessment of a change in a fluid, e.g. dilution or contamination thereof, or chemical change therein, which change alters the characteristics of the fluid with respect to transmission of radiation therethrough.

The invention is particularly applicable to the assessment of the concentration of a substance present in a fluid, the fluid being relatively transparent to radiation and the substance in the fluid causing an increasing resistance to the passage of radiation through the fluid as its concentration increases. The invention has been devised in relation to the situation wherein the fluid is a liquid and the substance therein is another liquid, such two liquids respectively being substantially transparent to visible light and resistant to the passage of visible light therethrough, such that increasing concentration of the latter liquid in the former liquid causes a progressive decrease in the transparency of the mixed liquids to light. However, it will be appreciated that the principle of the invention is also applicable when the substance whose concentration is required to be assessed is a solid which may form a solution or suspension in the liquid to cause a progressive decrease in the transparency of the liquid with increasing concentration of the solid. The principle of the invention is also applicable to mixtures of gases or vapours wherein a change in the concentration of one such gas or vapour in another causes a change in the transparency of the mixture to light or other radiation, or to the presence of particles in gases, e.g. smoke.

Some examples of applications of the invention are set forth hereafter, but the invention has been devised in relation to a requirement which exists in the medical field, namely that of assessing the quantity of blood contained in a liquid which otherwise comprises wholly or mainly water. A typical situation in which the requirement arises is that where surgery is performed on the prostate gland of a patient. It is important to know how much of the patient's blood is lost in order to assess the need for replacement thereof by transfusion, but direct measurement of such blood loss is extremely difficult because, although fluid can be collected by a catheter inserted into the bladder of the patient, such fluid comprises blood mixed with some urine from the patient's bladder and irrigation fluid, which is mainly water, introduced into the patient's bladder. The drained fluid, collected in a catheter bag, can be subjected to laboratory analysis to determine the concentration of blood therein, and thus the requirement for replacement of blood, but such analysis is time consuming and expensive. Furthermore, highly accurate analysis is not necessary for the immediate purpose of assessing the requirement for replacement blood. There is thus a requirement for a rapid and reasonably accurate assessment of the concentration of blood in the drained fluid to be made; then, since the total volume of fluid in a catheter bag is readily measured, it is possible to make a virtually immediate assessment of any requirement for blood replacement.

It is one object of the present invention to meet the above described requirement for assessment of concentration of blood in fluid drained from a patient. However, it will be appreciated that the principle of the invention, in meeting this requirement, is applicable far more widely, and examples of such application are referred to hereafter.

According to one aspect of the present invention, I provide apparatus for assessing a characteristic of a fluid in respect of its effect on the transmission of radiation through the fluid, comprising a chamber for receiving the fluid, said chamber including wall portions arranged for passage of radiation therethrough and through fluid therebetween and said wall portions being spaced differently from one another at different parts of the chamber so that the radiation travels different distances through the fluid, and means for examining the effect of transmission of the radiation through the fluid at said different parts of the chamber.

It will be appreciated that at a part of the chamber wherein the wall portions thereof are spaced at a greater distance from one another, compared with a part with a lesser spacing, the effect on the radiation being transmitted through the fluid between such wall portions will be greater. In particular, absorption of radiation by the fluid will be greater at a part of the chamber where the radiation has to travel a greater distance through the fluid. The position in the chamber at which absorption of radiation reaches a predetermined value provides an indication of the radiation-absorbing quality of the fluid.

Whilst it would be within the scope of the invention for the effect on transmission of infra-red or other radiation (possibly sound, e.g. ultrasound, or possibly a magnetic field) through the fluid to be examined, the invention conveniently makes use of the effect on visible light of transmission thereof through the fluid. For example, in the situation above referred to wherein the concentration of blood in an aqueous liquid is required to be assessed, an increase in the concentration of blood causes a decrease in the transparency of the liquid to visible light.

When the effect on transmission of visible light through the fluid is being examined, this may conveniently be assessed visually by a user of the apparatus. The apparatus may comprise means viewable through the wall portions of the chamber and the fluid contained therebetween, said means having a visible marking, e.g. a design, pattern, colour, or other characteristic adapted to be distinguishable to the user viewing it through the chamber, the arrangement being such that at some point in the chamber such marking will no longer be clearly visible to the user, dependent on the distance between the opposed walls through which the user is looking. The position in the chamber at which the marking ceases to be clearly visible to the user therefore provides an indication of the degree to which the fluid has had its light-transmitting ability reduced by contamination or otherwise.

The opposed wall portions of the chamber may have the spacing therebetween varying linearly, or in a curve or in some other manner, e.g. stepwise. For example, one wall portion may be planar while the other wall portion is in the shape of a curve, e.g. an exponential curve, approaching the first wall portion asymptotically from one end of the chamber to the other.

Preferably the apparatus is adapted to assess the concentration of a substance, which may be a solid or liquid, in a liquid. Thus the chamber may comprise, or form part of, a container adapted to have the liquid under investigation introduced therein and retained while a user carries out the assessment thereof.

A scale may be arranged along the chamber, adapted to provide a direct reading of concentration of the substance in the liquid in accordance with the position along the chamber at which the marking being viewed therethrough ceases to be clearly visible.

For the elimination or reduction of possible errors in looking through the chamber by the user, due to refraction at the wall portions thereof particularly if one such wall portion is curved, the chamber may be defined by a dividing wall portion provided in a container having substantially parallel opposite walls. Thus the container is divided into said chamber for receiving the fluid to be assessed, and a further chamber which preferably contains the uncontaminated fluid in which the concentration of the contaminating fluid is to be assessed.

Conveniently the container, including the dividing wall portion therein defining the two chambers, is a one-piece moulding of plastics material which is substantially transparent to visible light. The marking for observation by the user, and/or the scale, may be provided on such container, or on another element adapted to be held or supported in relation to the container so as to be visible therethrough. It is envisaged that such apparatus according to the invention may be a "throw-away" item, intended to be used once only.

As above referred to, the invention has been devised for use in connection with the carrying out of a surgical operation. It is envisaged that apparatus according to the invention may be incorporated in or provided in operative association with a disposable catheter or catheter bag, and according to another aspect of the invention I provide a catheter or catheter bag having apparatus according to the first aspect of the invention provided in operative association therewith, for assessing liquid flowing through or contained in the catheter or bag, respectively.

Other features which may be provided in apparatus according to the invention are referred to in the following description with reference to the drawings.

According to another aspect of the invention, I provide a method of assessing a characteristic of a fluid in respect of its effect on the transmission of radiation through the fluid, comprising passing radiation through the fluid in a chamber having wall portions which are spaced differently from one another at different parts of the chamber so that the radiation travels different distances through the fluid at such parts of the chamber, and examining the effect of transmission of the radiation through the fluid at said different parts of the chamber.

Preferably the radiation is visible light, and the method comprises visual observation through the chamber and fluid therein of a viewable element, and observing the position in the chamber at which such viewable element is no longer clearly discernible, such position providing an assessment of the relevant characteristics of the fluid.

Preferably the method is that of assessing the concentration of a substance in the fluid, the substance being one of which an increase in concentration thereof in the fluid causes a decrease in the transparency of the fluid to visible light.

The substance may be a first liquid, and the fluid a second liquid.

Further examples of applications of the invention include assessing contamination of cleaning fluids or of lubricants, e.g. engine oil. It is envisaged the invention will have application in the food industry, e.g. in the analysis of mixtures, e.g. milk/cream/water. The invention also has application to measurement of concentration of solutions, e.g. antifreeze or a dye, or in cases where a chemical reaction or test involving a chemical reaction produces a colour change in a liquid. Examples of such latter include measurement of pH of a liquid involving a colour-changing indicator, or enzyme linked assays, e.g. immuno assays.

The invention will now be described by way of example with reference to the accompanying drawings, of which:

Figure 1:
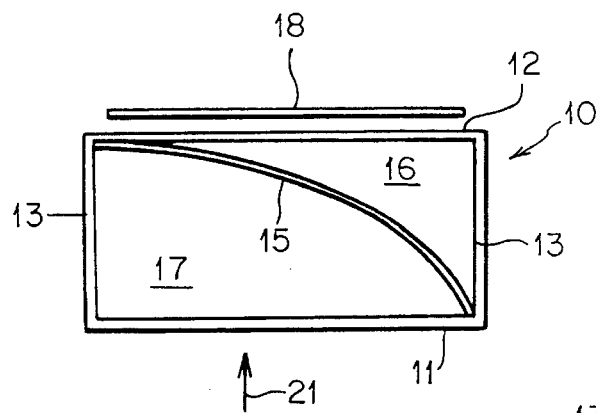
FIGS. 1 and 2 are respectively a plan view and a front elevation of a first embodiment of apparatus according to the invention.
Figure 2:
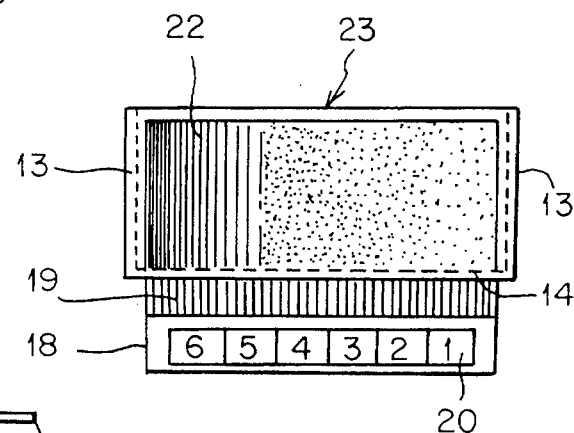

Referring firstly to FIGS. 1 and 2 of the drawings, the embodiment of apparatus according to the invention shown therein is intended for assessing the concentration of a first liquid in a second liquid, the second liquid being substantially clear or not presenting any obstacle to transmission of light therethrough and the first liquid being, at least when present in the form of more than a layer of minimal thickness, substantially opaque to light of the intensity typically ambient in a working environment. By way of example, as in the example first referred to herein, the first liquid may be blood and the second liquid may be a clear aqueous solution, and it will be appreciated that as the concentration of blood in the clear liquid increases the resulting mixture of liquids becomes progressively less clear and more resistant to the passage of light therethrough. At a given concentration of the first liquid in the second liquid, transmission of light through the mixture of liquids decreases the greater is the distance that the light has to travel through the mixture of liquids.

The apparatus shown in FIGS. 1 and 2 comprises a container 10 which is generally of rectangular configuration both in elevation and plan, comprising a front wall 11; a rear wall 12; which walls are substantially parallel to one another and planar; opposed end walls 13; and a base wall 14. Between opposite corners of the container, in plan view, there extends a partition 15 which divides the interior of the container into a first chamber 16 and a second chamber 17. In the embodiment illustrated, the partition 15 is of curved shape, e.g. an exponential curve, and approaches the rear wall 12 asymptotically so that the chamber 16 has a front to rear dimension which is a minimum at one end of the container increasing at an increasing rate as the other end of the container is approached.

At least the front wall 11, rear wall 12 and partition 15 of the container are of a transparent material, and conveniently the entire container and the partition therein may be formed as a moulding of a suitable transparent plastics material.

Behind the rear wall 12 of the container there is disposed an element 18 which is flat and which carries on its surface facing the rear wall 12 a pattern which is designed to be readily visible. As illustrated in FIG. 2, this comprises a number of dark vertical lines 19 on a light background. Extending along the length of the element 18 there is also a scale 20 of graduations.

The mode of use of the apparatus according to FIGS. 1 and 2 is that there is introduced into the chamber 16 the mixture of the first and second liquids whose relative concentration is required to be assessed. The chamber 17 is filled with the second liquid which does not contain any of the first liquid. The user of the apparatus then looks through the container from its front wall 11 to the element 18 behind the rear wall 12 thereof, in the direction of arrow 21. To the user, there will be a part of the container, at the end thereof at which the chamber 16 is of minimum front to rear dimension, at which the markings 19 on the element 18 are clearly visible as indicated at 22. At some region approaching the opposite end of the container, because the user has to look for a greater distance through the mixed liquids in the first chamber 16, the markings 19 will not be discernable. In practice, it has been found that there is a relatively well defined region 23 at which the markings 19 become discernable due to the decreasing dimension of the chamber 16. It will be appreciated that the exact position of the region 23 along the container 10 therefore represents a measure of the concentration of the first liquid in the second liquid, which may be read off the scale 20 to provide a measure which is sufficiently accurate for many purposes such as described above.

As illustrated, the element 18 is disposed behind the rear wall 12 of the container 10. It is envisaged that the container 10, which as referred to above is conveniently a plastics moulding, will be in the nature of a "throw-away" item, to be discarded after the carrying out of an assessment, and the element 18 may take the form of a card which may simply be held at the rear wall 12 of the container by a user. For carrying out tests on different liquids, or on different relative concentrations of liquids, a range of different such cards may be provided, from which the user selects an appropriate one according to the nature of the liquids involved. For example, such cards may differ in respect of the scale 20, or in respect of the design or pattern 19 they bear to suit different colours of liquid.

Alternatively, a visible pattern or design, and scale, could be printed on the rear wall 12 of the container.

Another way in which the apparatus may be adapted for carrying out tests on different liquids, or on different relative concentrations of liquids, is to provide an additional element between the element 18 and the rear wall 12 of the container 10, which additional element has a visual characteristic changing along its length. For example, such additional element may be clear at one end and opaque at the other end, or coloured at one end and uncoloured at the other end, thereby changing the effective aspect of the element 18. Yet another possibility is that the rear wall 12 of the container may have a visual characteristic changing along its length.

The chamber 17 which contains uncontaminated liquid acts as a lens and helps prevent any refraction errors in use of the apparatus.

Figure 3:
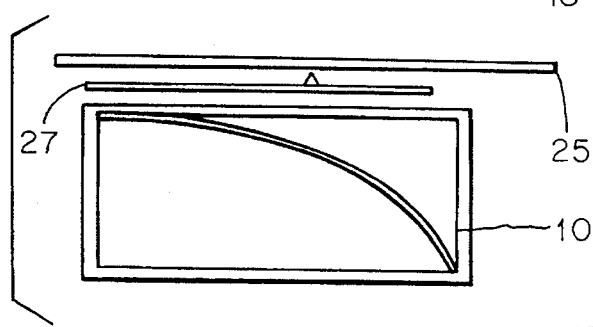
FIGS. 3 and 4 are respectively a plan view and a front elevation of a further embodiment of apparatus according to the invention.
Figure 4:
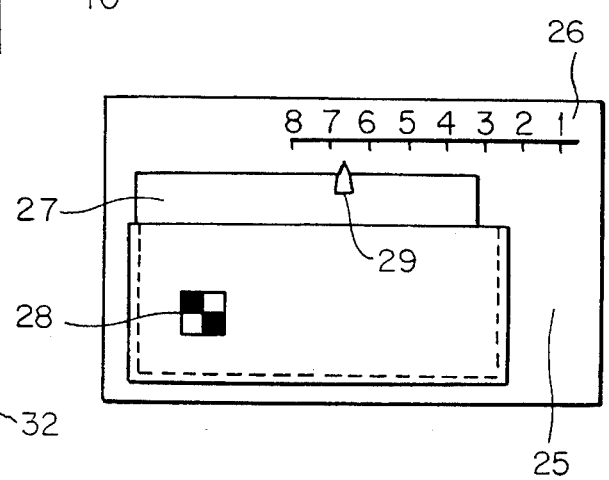

Referring now to FIGS. 3 and 4 of the drawings, these show a modified embodiment of the apparatus. This embodiment comprises a container which is of the same configuration as the container 10 in FIGS. 1 and 2, behind which there is disposed a fixed element 25 which bears a scale 26 and, between the element 25 and the rear wall of the container, a member 27. The member 27 is disposed between the container and the element 25, and is supported for movement lengthwise of the container. The member 27 bears a visible pattern 28 and a pointer 29 against which the scale 26 may be read.

In use of the apparatus of FIGS. 3 and 4, the two chambers of the container 10 will be filled respectively with the contaminated liquid being assessed and with the uncontaminated clear liquid, as in the embodiment of FIG. 1. The user then looks through the container and moves the member 27 lengthwise of the container until it reaches a position at which the pattern 28 is no longer discernable. The pointer 29 then provides a reading, off the scale 26, of the relative concentration of the two liquids.

Figure 5:
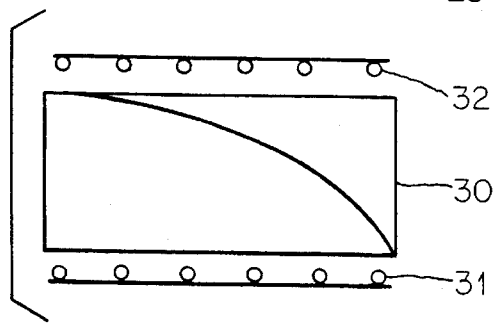
FIG. 5 is a diagrammatic plan view of a further embodiment of apparatus according to the invention.

Referring now to FIG. 5 of the drawings, this shows a further embodiment of apparatus which includes a container 30 which is of the same configuration as the container 10 in FIGS. 1 to 4. At the front and rear of the container there are disposed respective arrays of radiation-emitting elements 31 and radiation receiving elements 32. By way of example, such radiation may be infra-red radiation. Depending on the relative concentration of the liquids in the mixture thereof, a greater or lesser number of the receiving elements 32 will respond to the radiation transmitted through the container, thereby providing a direct assessment of such relative concentration. Assessment using such apparatus may readily be automated using well-known electronics principles.

Figure 6:
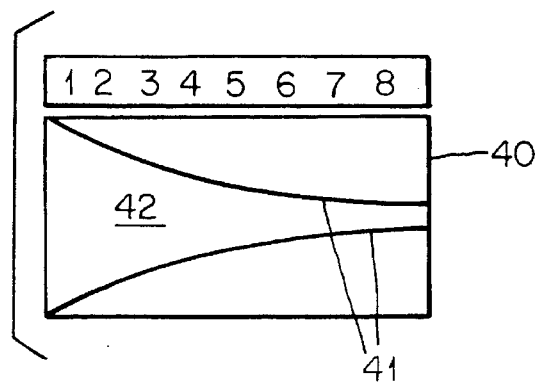
FIGS. 6 and 7 are diagrammatic plan views of yet further embodiments of apparatus according to the invention.

Referring now to FIG. 6 of the drawings, this shows in plan view a container 40 which has two internal partitions 41 to define a chamber 42 therein for receiving a liquid under investigation. The chamber 42 is thus positioned symmetrically between the front and rear walls of the container 40.

Figure 7:
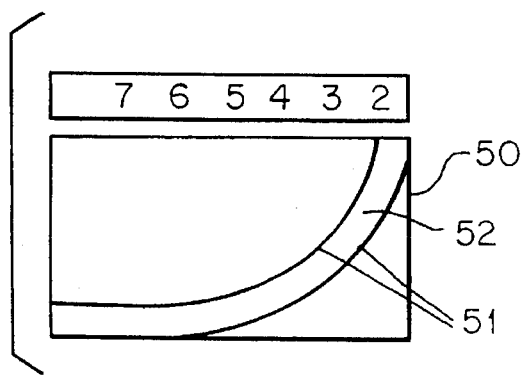

FIG. 7 shows a container 50 which is divided by two internal partitions 51 to form a chamber 52 for fluid under investigation. The shape of the partitions 51 is such that the cross sectional area of the chamber 52 varies only slightly from one end of the container to the other, thereby providing a substantially constant resistance to flow of fluid through the chamber 52 throughout the length of the chamber. When the container is viewed from front to rear, however, the dimension of the chamber 52 is substantially greater at one end of the container than at the other end. Therefore the apparatus may be used in the same manner as described above, but with potential advantages in the case where a moving stream of fluid is being examined.

Figure 8:
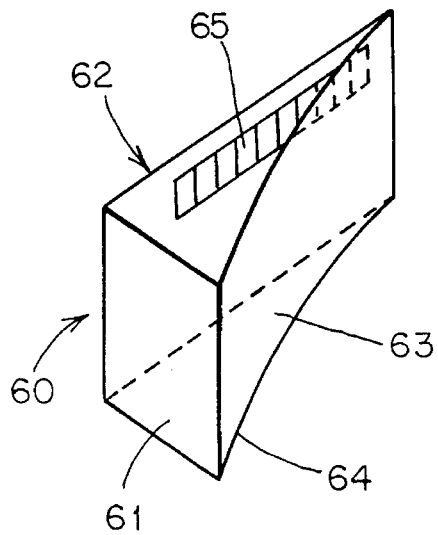
FIG. 8 is a diagrammatic perspective view of another embodiment of apparatus according to the invention.

Referring now to FIG. 8 of the drawings, there is shown an embodiment of the invention which is of somewhat simplified construction compared with the embodiments above described. It comprises a container 60 which is of somewhat wedge-shaped configuration in plan view, comprising a side wall 61, a rear wall 62 and a front wall 63 which may be curved in similar configuration to the partition 15 in the embodiment of FIGS. 1 and 2. The container has a closed base 64 and an open top for enabling a liquid for assessment to be introduced into the chamber defined by the container. A scale 65 is printed on or adhered to the rear wall 62. A means for assisting the visual assessment, e.g. a suitable pattern or the like, may be provided in addition to the scale 62.

Apparatus according to FIG. 8 is used in substantially the same manner as described above in relation to the other Figures of the drawings.

For use of apparatus according to the invention in the course of a surgical operation, as above referred to, it is envisaged that the apparatus may be incorporated in or provided in operative association with a disposable catheter or catheter bag. For example, the apparatus may be provided internally of a transparent catheter bag, arranged so that liquid contained in the bag can enter the chamber of the apparatus and the user can look through the apparatus to assess the liquid contained therein. Alternatively, the apparatus could be provided externally of a catheter bag, there being provided means affording a connection for flow of liquid from the catheter bag into the chamber of the apparatus. A further possibility is that all or part of a quantity of liquid flowing through a catheter may be arranged to flow through the chamber of the apparatus.

Figure 9:
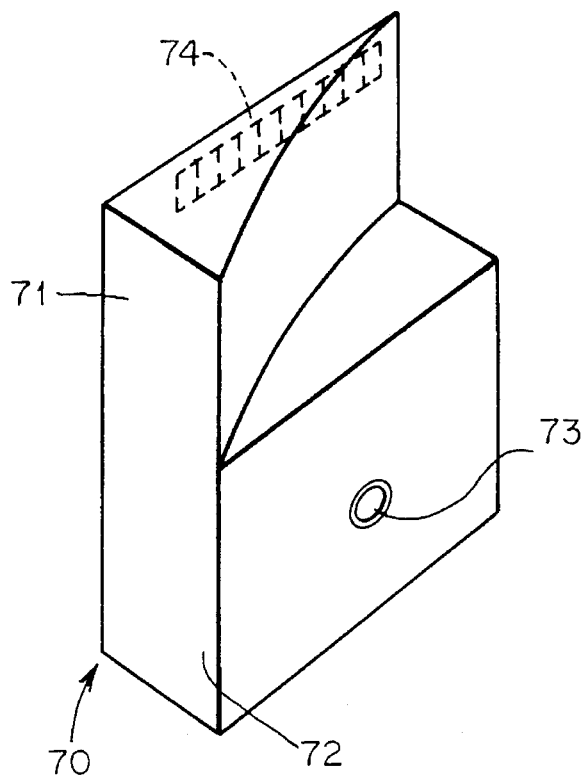
FIG. 9 is a diagrammatic perspective view of yet a further embodiment of apparatus according to the invention.

Referring now to FIG. 9 of the drawings, this shows an embodiment of the invention which is adapted to carry out a particular assessment, namely that of estimating the haemoglobin concentration in the blood of a patient. The apparatus comprises a closed container 70 of which a portion, 71, is in the configuration of the device shown in FIG. 8 but with a closed top and open bottom, and a portion 72 is generally of rectangular configuration in elevation and plan, communicating with the container portion 71. Together, the two portions of the container define a chamber whose total volume may be approximately 50 ml. One wall of the container, e.g. as illustrated part of the portion 72, is provided with an injection port 73 which may be in the form of a diaphragm, e.g. of rubber, enabling introduction of a liquid into the interior of the container by use of a hypodermic syringe.

Apparatus as shown in FIG. 9 would be supplied filled with a dilutant liquid, e.g. a saline solution. A measured quantity of patients blood would be injected into the apparatus through the port 73, e.g. 0.2 ml of blood. To mix the blood thoroughly with the saline solution, the apparatus would be agitated and it may contain a movable agitator member, e.g. a plastics ball or the like to assist mixing. The part 71 would then be looked through and the scale 74 observed in the manner above described, to provide an indication of haemoglobin concentration. When apparatus is supplied specifically for such a test, the scale 74 could be calibrated directly in haemoglobin concentration, e.g. in grams/100 ml.

The features disclosed in the foregoing description, or the following claims, or the accompanying drawings, expressed in their specific forms or in terms of a means for performing the disclosed function, or a method or process for attaining the disclosed result, as appropriate, may, separately or in any combination of such features, be utilised for realising the invention in diverse forms thereof.

I claim:

1. Apparatus for assessing a characteristic of a fluid in respect to its effect on transmission of visible light through a fluid, comprising a chamber for receiving the fluid, said chamber including front and rear wall portions transparent to visible light and arranged for passage of visible light therethrough and through fluid therebetween, said front and rear wall portions being spaced differently from one another at different parts of the chamber so that visible light travels different distances through the fluid, and means viewable by a user through at least said front wall portion of the chamber and the fluid contained therebetween, said viewable means being disposed at a fixed position generally adjacent to and generally along the length of said rear wall portion and having a visible marking adapted to be distinguishable to the user viewing it for examining the effect of transmission of visible light through the fluid at said different parts of the chamber.

2. An apparatus according to claim 1, wherein said wall portions are positioned opposite one another and said spacing between said wall portions of the chamber varies non-linearly.

3. Apparatus according to claim 2, wherein at least one of said wall portions of the chamber is of curved configuration, approaching another wall portion asymptotically from one end of the chamber to the other.

4. Apparatus according to claim 1, wherein said chamber comprises or forms part of a liquid-tight container for retaining a fluid during the assessment of its characteristics.

5. Apparatus according to claim 1 comprising a graduated scale disposed along at least a part of a wall portion to provide a direct reading of concentration of a substance in the fluid.

6. Apparatus according to claim 1 wherein at least said chamber is made from a one-piece molding of plastic material.

7. Apparatus according to claim 6, wherein a marking for observation by the user is provided on a wall portion of said plastics molding.

8. Apparatus according to claim 4, wherein said container includes at least two portions, a first portion defining said chamber and a second further portion attached to said first portion in communication with said chamber, so that together said portions define a predetermined volume.

9. Apparatus according to claim 8, wherein said container contains a dilutant liquid and also comprises means for introduction of a further fluid for assessment of its characteristics into said dilutant liquid.

10. Apparatus according to claim 1, wherein said apparatus includes a catheter and said viewable means is attached to said catheter.

11. Apparatus for assessing a characteristic of a fluid in respect to its effect on transmission of visible light through a fluid, comprising a chamber for receiving the fluid said chamber including front and rear wall portions transparent to visible light and arranged for passage of visible light therethrough and through fluid therebetween, said front and rear wall portions being spaced differently from one another at different parts of the chamber so that visible light travels different distances through the fluid, and movable viewable means viewable by a user through the wall portions of the chamber and the fluid contained therebetween, said viewable means being disposed generally adjacent to and movable generally along the length of said rear wall portion and having a visible marking adapted to be distinguishable to the user viewing it for examining the effect of transmission of visible light through the fluid at said different parts of the chamber.

12. Apparatus according to claim 11, wherein a marking for observation by the user is provided on an element adapted to be held in relation to the chamber so as to be visible therethrough.

13. Apparatus for assessing a characteristic of a fluid in respect to its effect on transmission of visible light through a fluid, comprising a first chamber for receiving the fluid, said first chamber including a first and a second wall portion transparent to visible light and arranged for passage of visible light therethrough and through fluid therebetween, said first and second wall portions being spaced differently from one another at different parts of said first chamber so that visible light travels different distances through the fluid, and means viewable by a user through the first and second wall portions of said first chamber and the fluid contained therebetween, said viewable means having a visible marking adapted to be distinguishable to the user viewing it for examining the effect of transmission of visible light through the fluid at said different parts of said first chamber, said apparatus further comprising a third wall portion joined to said first wall portion so as to form a second chamber for containing uncontaminated fluid and arranged so that visible light travels through the uncontaminated fluid and the fluid to be assessed.

14. A method of assessing a characteristic of a fluid in respect to its effect on transmission of visible light through the fluid, comprising passing visible light through fluid contained in a chamber having front and rear wall portions which are transparent to visible light and arranged for passage of visible light therethrough and through fluid therebetween, said front and rear wall portions being spaced differently from one another at different parts of the chamber and so arranged that said visible light travels different distances through the fluid at such parts of the chamber and further comprising visual observation through the chamber and fluid therein of a viewable element being disposed at a fixed position generally adjacent to and generally along the length of said rear wall portion and observing the position in the chamber at which such viewable element is no longer clearly discernible on a graduated scale, such position providing an assessment of said characteristics of the fluid.

15. A method according to claim 14 for assessing the concentration of a substance in a fluid, the presence of said substance in the fluid causing a decrease in transparency to visible light.

16. A method according to claim 15, wherein said substance is a liquid.

17. A method according to claim 16, wherein said substance is blood.

* * * * *